United States Patent [19]

Berlin et al.

[11] 4,220,161
[45] Sep. 2, 1980

[54] PERTURBATION DEVICE FOR THE MEASUREMENT OF AIRWAY RESISTANCE

[76] Inventors: Howard M. Berlin, 2 Colony Blvd., Apt. 123, Wilmington, Del. 19802; Arthur T. Johnson, R.D. 2, Box 32, Darlington, Md. 21034

[21] Appl. No.: 569,345

[22] Filed: Apr. 18, 1975

[51] Int. Cl.³ .............................................. A61B 5/08
[52] U.S. Cl. .................................................. 128/720
[58] Field of Search .................... 128/2.08, 2.07, 2 C, 128/DIG. 29, 720, 719, 716; 73/211

[56] References Cited

U.S. PATENT DOCUMENTS

| 3,036,569 | 5/1962 | Clements | 128/2.08 |
| 3,621,833 | 11/1971 | Crane | 128/2.08 |
| 3,857,385 | 12/1974 | Hampl | 128/2.08 |

FOREIGN PATENT DOCUMENTS

| 1119459 | 12/1961 | Fed. Rep. of Germany | 128/2.08 |
| 2233829 | 7/1972 | Fed. Rep. of Germany | 128/2.08 |
| 850750 | 10/1960 | United Kingdom | 128/2.08 |

Primary Examiner—Lee S. Cohen
Attorney, Agent, or Firm—Nathan Edelberg; Robert P. Gibson; Kenneth P. Van Wyck

[57] ABSTRACT

Instrumentation and process of measuring human airway resistance at rest or during physical activity.

5 Claims, 6 Drawing Figures

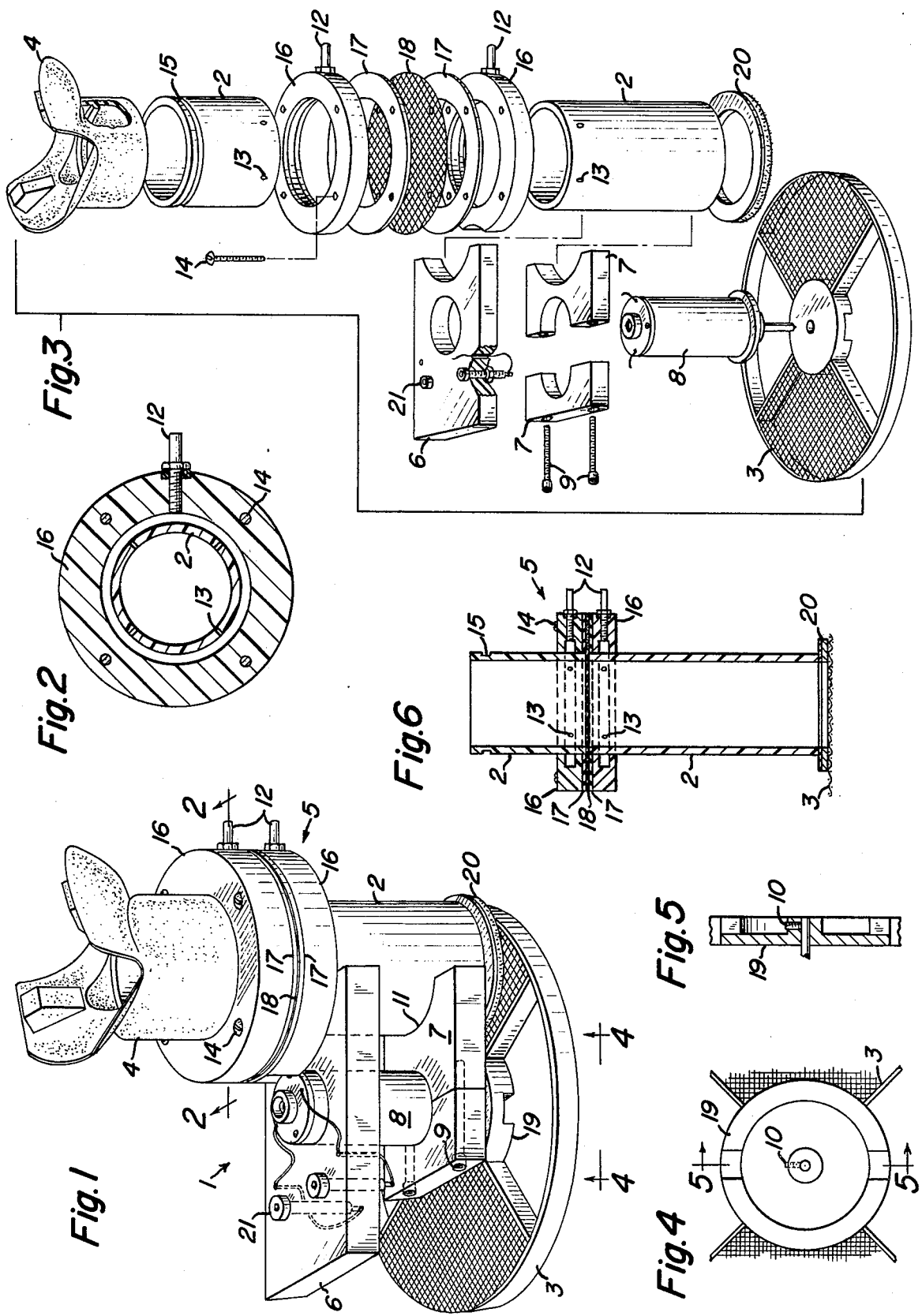

PERTURBATION DEVICE FOR THE MEASUREMENT OF AIRWAY RESISTANCE

DEDICATORY CLAUSE

The invention described herein may be manufactured, used or licensed by or for the United States Government for governmental purposes without the payment to me of any royalty thereon.

BACKGROUND OF THE INVENTION

Our invention deals with a new process and device for measuring human subject (breathing) airway resistance for medical, diagnostic, and other testing and evaluation purposes.

Devices and techniques are known to those in pulmonary allied investigatory fields to enable some knowledge to be had of subjects and patients, however, in each instant the results have been proven unreliable. The unreliability stems from the fact that no valid method exists to measure separately and directly airway resistance in man. Until our invention, the esophageal balloon and pneumotachograph, the plethysmograph, forced pressure oscillations, and airway interrupter methods were used to measure respiratory flow resistances. A comparison of these four methods can be found in an article by Frank, Mead and Whittenberger, entitled "Comparative sensitivity of four methods for measuring changes in respiratory flow resistance in man" and published in the Journal of Applied Physiology, Vol. 21, No. 6, Dec. 1971. The esophageal technique involves the use of a balloon which is lowered into the esophagus by way of the nose passage. Also, a pneumotachograph is used to measure flow at the mouth. This method cannot be used by untrained subjects and requires correction due to lung compliance. Moreover, conditions of test such as subject exercise are nearly excluded and/or prohibitive.

The plethysmographic method, developed by Dr. DuBois et al involves the use of a huge box. This is called a body plethysmograph which is essentially an airtight box used to apply Boyles law relating to gas volumes and pressures which has been used for lung and abdomen work. Herein, the subject sits wearing a nose clip. He breathes within this confined environment on and into a permanently fixed mouth apparatus to which is connected external test gear. So also, to accomplish the test cycle the subject must simulate rapid inhalation and exhalation by panting. Aside from the above drawbacks, exercise within the box is prohibitive.

The method of forced pressure oscillations measures flow resistance of the lungs plus chest wall, viz, total respiratory resistance. Here, by the "chest wall" is meant all those tissues that are lined internally by the parietal pleura and incapsulate the lungs. This technique is a modified DuBois et al method which uses the plethysmograph. The subject breathes quietly as the pressure oscillations are applied at the mouth.

The interrupter method by Clement et al is substantially a method of estimating flow resistance based upon repetitive interruption of airflow while the subject breathes in an alinear flow meter. It is an indirect way of measuring airway resistance. Substantially it involves the rapid equilibrated pressure at the mouth following sudden obstruction of flow taken regularly as a measure of the nonelastic component of transpulmonary pressure. It depends upon the assumption that pressures recorded at the mouth rise to equal alveolar pressure (as altered) when motion of air ceases, and that intrapleural pressure does not appreciably change as a result of airflow interruption.

This method is expected to measure the sum of the airway and lung tissue resistance. However, it too has shortcomings. In the above alluded to comparisons, these learned persons found that for unknown reasons the method tends to overestimate total pulmonary flow resistance in healthy subjects and to underestimate flow resistance in obstructive disease.

The above shortcomings have been and were the stimulus for we inventors to bring forth our invention. It overcomes some of the above-mentioned to now for the first time enable the small researcher, the experimentor and the physician to have at his ready disposal an inexpensive process and device for measuring airway resistance in the testing, checking, prevention, and diagnosis of disease in and about the lung areas.

SUMMARY

Briefly, our invention deals with a modified interruptor process and a new and unobvious device to use therewith. In the interrupter aforementioned, airflow is totally interrupted, whereas, with our process and device it is merely perturbed. That is, the device switches respiratory airflow from one known resistance to another, with the difference between resistance values as small as current measurement techniques will allow. Flow and mouth pressure are simultaneously measured, for example, under both resistance conditions. Our new process and device does not force the measurement from one extreme to the other as is done in the interrupter method. This from an engineering and technical standpoint is unsound. Moreover, our tests substantiate such a proffer. The interrupter system abruptly stops flow and then starts it, whereas, our invention process and device provide for a simple portable and unobvious approach of modification by degree rather than by kind. That is, building up unwanted vibration, and unwanted heterogenous spurts and releases of pressure do not contribute to inaccurate results with our process and device. Moreover, start and stop flow as is the case with the interrupter method has an extreme effect upon the respiratory system. In our system, perturbation of airflow is kept to a minimum which contemporaneously benefiting from portability and adaptability had from the above alluded to interrupter system. With our invention esophageal pressure, at least, does not change while our device is in operation, whereas with the interrupter process esophageal pressure changes exist.

Our invention device and process provide a cyclic or alternating high and low resistance to airflow at the mouth and, so also, provide a means of measuring pressures thereat. The varying impedance or resistance of a cyclic nature is provided by a rotating wheel-like member with two distinct passages. The wheel is rotatably affixed, so that, it can upon revolution, modify the airflow passage to increase or decrease resistance thereof. The air passage is in the form of a tube terminated on one end by a mouth piece and the other end thereof by said wheel. Intermediate thereof, we have interposed a conventional pneumotachometer to enable us to measure airflow rate and the mouth pressure. For operating efficiency, of course, the subject must use a nose clamp. Our apparatus can be handheld or affixed to the body while exercising, for testing, diagnosis, etc., if desired.

Once we take measurements, as aforementioned, we can determine the flow measurement or mouth pressure measurement, if desired. These values can then be used to set standards, parameters for patient screening and diagnostic purposes and for further pulmonary research and investigatory purposes.

Advantages, therefore, of our new and unobvious airway resistance measuring process and device enable reliable and repetitive results in the areas heretofore discussed.

It is therefore an object of our invention to provide a new process and device for pulmonary function testing.

Another object of our invention is to provide a new process and device for measuring human subject airway resistance.

Still another object of our invention is to provide a new process and device for non-invasively measuring airway resistance.

Another still further object of our invention is to provide a noninvasive measurement of human subject airway resistance by parameters set without completely interrupting airflow.

Other and further objects of this invention will be more apparent to those skilled in the art from the following detailed description of the annexed drawings which by way of that set out below illustrate at least one example of our invention, device, and process.

BRIEF DESCRIPTION OF THE DRAWINGS

FIG. 1 is an isometric view of our perturbation measuring device.

FIG. 2 is a section view of the pneumotachometer showing a tap off terminal.

FIG. 3 is an exploded view of the FIG. 1 device.

FIG. 4 is a partial section of our unique variable airflow resistance wheel.

FIG. 5 is a section of the hub area of FIG. 4.

FIG. 6 is a section through the air passage, mouth area, and variable airflow wheel of our invention of FIG. 1.

DESCRIPTION OF THE INVENTION

FIG. 1 depicts our invention perturbation device 1. It comprises tubular airpassage member 2 cyclically closed at one end by rotatable variable resistance wheel 3 and terminated at the other extreme end with mouthpiece 4. Shown concentrically disposed and fixed upon member 2 is airflow meter 5. It is understood, of course, that this specific airflow meter 5 design need not be used. A multitude of configurations would occur to one skilled in the art, hence, applicants do not desire to be limited thereby. Attached to airpassage tube 2 is two part bracket or support assembly 7 and terminal support member 6. Both assembly 7 and support 6 act to securely hold motor 8 in fixed relation to airpassage 2. Motor 8 to which resistance wheel 3 is affixed by screw 10 is manufactured by the Globe Industries, Inc., Dayton, Ohio, and is a 27 volt dc. motor with a part number 43A199-3. However, any motor which will rotate resistance wheel 3 at a prescribed constant angular velocity will suffice. Assembly 7 and member 6 are accurately configured to compliment the external configuration of airpassage tube 2 and are secured thereat by resin or adhesive 11 of epoxy material, for example. This is so because all elements here are plastic. Screws 9 securely sandwich the housing of motor 8 in fixed position by forcing portions of assembly 7 together.

FIG. 2 shows in cross section airflow meter or pneumotachmeter 5 with pressure tap 12. Apertures 13 provide pressure access to tap 12 from within air passage tube 2. Pressure tap 12 is fashioned from 13 gauge hypodermic needles having luer fittings. The through passage in tap 12 is not depicted. Screws 14 shown in section secure the components of the airflow a pneumotachometer 5 together.

FIG. 3 shows typical mouth piece 4 removed from tube portion 2 for clarity. The groove 15 in tube portion 2 aids in holding mouth piece 4. Because the mouth piece 4, made of rubber or resilient plastic, can be equipped with an inturned lip or ridge or protrusion to compliment groove 15. Airflow or pneumotachometer 5 comprising sections 16 of plexiglass and rubber gaskets 17 each sandwiching 50 mesh screen 18 and secured by bolts or screws 14 are shown in expanded view for clarity. Portions 2 of the airpassage tube 2 are secured, to section 16 with adhesive or resin, so that a sealed assembly is had. Resilient seal 20 of rubber or resilient plastic 5 seals wheel 3 to tube 2.

FIGS. 4 and 5 are partial views of resistance wheel 3 with only hub portion 19 set out. Note here screw 10 shows how the hub 19 is affixed to motor 8 shaft.

FIG. 6 is a section through airpassage 2 and airflow meter 5. Note here seal 20 is shown in proper perspective performing its function.

In operation our device 1 of FIG. 1 is simple to operate. Resistance wheel 3 of four quadrants; i.e., two without obstruction and two with 50 mesh screen is made of stainless steel to which is soldered the screen portions. Wheel 3 is rotated by applying 24 volts D.C. or less at terminals 21 to cause motor 8 to rotate. The speed the resistance wheel rotates is commensurate with the respiration rate and can be chosen such that very little lung volume change occurs between the unimpeded and impeded flow. The resistance of the resistance portions of wheel 3 is 0.275 cm $H_2O$-sec/liter at 85LPM and was chosen to give us a usable recorder signal and yet be as unnoticeable to the subject as possible.

The airpassage tube 2 and the airflow meter 5 are of "plexiglass" or of other known plastic. Also, member 6 and assembly 7 can be of plastic, as well. Alternatively, all of the above can be of metals, for example. The one critical factor is that each component perform its desired function. Hence, a combination of metals and plastics would work as well. So also, the resistance wheel could be of metal or plastic, if desired, and could be cast or molded with the proper impeded areas, etc.

To operate our device of FIG. 1 voltage is applied to terminals 21 to cause motor 8 to turn thereby rotating wheel 3. Note, by referring to FIG. 6 and FIG. 1, we see wheel 3 overlays the end of tube 2 so that variable resistance is had by wheel 3 rotation. It rotates at approximately ten times the respiration rate of a subject. To insure that utility is given to our apparatus two pressure transducers by the Validyne Corp., for example (now shown) are used. One is connected to the respective terminals 12 of airflow meter 5. It then measures the airflow in liters/sec. Connected to terminal 12 closest to the mouthpiece side of the pneumotachometer is one leg of a second pressure transducer (not shown), its other leg is left to measure the atmosphere. From these transducers, values are fed to other recording and indicating apparatus. Here we use an oscillographic recorder of conventional make for this purpose. Once the transducers are connected, the process can be practiced.

Subject annalysis is had by having the subject hold device 1 while inhaling and exhaling through mouthpiece 4, while being careful not to jar or disturb, by abrupt movements, the apparatus 1. For this reason, if desired our device can be modified by having connections to tube 2 at 13 carried off to a remote location to an airflow meter. As the subject breathes normally (with a nose clip on) through mouthpiece 4, variations of airflow and mouth pressure are noted with time on the above-mentioned oscillographic recorder, not shown. With the above data accumulated, airway resistance can be calculated by one of the following alternative ways:

(1) FLOW MEASUREMENT $$R_{aw} = \frac{R_s}{\left(\frac{\dot{V}_O}{\dot{V}_S} - 1\right)} - R_{pt}$$

(2) MOUTH PRESSURE MEASUREMENT $$R_{aw} = \frac{R_{pt}\left(\frac{P_{ms}}{P_{mo}} - 1\right)}{1 - \frac{P_{ms}}{P_{mo}}\left(\frac{R_{pt}}{R_{pt} + R_s}\right)}$$

where:
$R_{aw}$—airway resistance, cm $H_2O$-sec/L
$R_{pt}$—pneumotachomter resistance, cm $H_2O$-sec/L
$R_s$—wheel screen resistance, cm $H_2O$-sec/L
$P_m$—mouth pressure, cm $H_2O$
$\dot{V}$—airflow, L/sec
o,s—subscripts referring to open and screen.

Further process and device background information on our invention can be found in the publication "Medical Instrumentation", Vol. 8, No. 2, page 141, published and publically presented in New Orleans, Louisiana on Apr. 19, 1974.

One real unique advantage to our system and device is that either mouth pressure or airflow can be measured at tap 12 of airflow meter 5 and that both need not be measured. Comparing our process with that of the interrupter method it is readily seen that the interrupter method must simultaneously test both mouth pressure and also airflow. Notwithstanding, the deleterous effects of the interrupter method outlined above as our tests indicate and for the reasons advanced, reliability in the pulmonary testing and diagnostic area is now finally had with the use of our process and device.

Our device, as is set out above, can take diverse forms, it can be formed as one unitary casting or molding of either metal or plastic or a combination of the materials without departing from our invention. The resistance imposed can also be achieved by reciprocation, or electronic or machanical shutters, etc., for example, without departing from our invention.

To practice our process we essentially place our device 1 in series with the respiratory system of a breathing animal. It should be noted that our device can be used on any breathing thing, not only humans.

In summary, we want it understood that our device and process can take many forms and involve different steps and we do not want to be limited to only those things described but only to the metes and bounds defined by the appended claims.

We claim:
1. An airway resistance measuring device for animals comprising:
    an air passage means providing air passage for an air stream from the animal to the atmosphere;
    a cyclic perturber means affixed to said passage means for cyclically imposing a resistance to said air stream comprising a sectored member traversing said passage means on one end thereof and said sectored member having at least one sector with a large void and at least one sector having plural small voids, and a drive means affixed to said passage means for driving said sectored member to alternately impose said sectors across said passage means; and pressure measuring means affixed to said passage means for measuring disparities caused by the resistance.
2. The invention of claim 1 wherein said sectored member is a rotatable wheel and wherein said plural small voids are formed with screen means acting as said resistance.
3. The invention of claim 2 wherein said passage means includes a mouth piece.
4. The invention of claim 2 wherein said pressure measuring means includes an airflow meter.
5. The invention of claim 1 wherein the pressure measuring means is tap means for connecting a remotely located airflow means.

* * * * *